(12) United States Patent
Dennis et al.

(10) Patent No.: US 6,812,375 B2
(45) Date of Patent: Nov. 2, 2004

(54) PRESSURE-EVENIZING LOW-REBOUND WOUND DRESSING

(76) Inventors: Michael R. Dennis, 50900 W. Dike Rd., Scappoose, OR (US) 97056; Michael W. Tucker, 7565 SW. 149th Ave., Beaverton, OR (US) 97007; Gerhard Paasche, 53797 West Lane Rd., Scappoose, OR (US) 97056

( * ) Notice: Subject to any disclaimer, the term of this patent is extended or adjusted under 35 U.S.C. 154(b) by 123 days.

(21) Appl. No.: 10/174,886

(22) Filed: Jun. 19, 2002

(65) Prior Publication Data

US 2003/0236479 A1 Dec. 25, 2003

(51) Int. Cl.$^7$ .......................... A61F 13/00; A61G 9/00; E03G 5/09
(52) U.S. Cl. ................ 602/53; 602/41; 602/42; 602/43; 2/455; 2/456; 2/411
(58) Field of Search ............................. 2/455, 456, 411, 2/412, 414, 425, 181.2, 6.6, 410, 16, 22, 24, 466, 459, 162, 170; 428/304.4, 318.8, 423.1; 36/313, 28, 29; 602/41–59, 60, 61, 69, 79; 128/112.1, 117.1, 816, 817, 878, 882; 607/96, 108–112

(56) References Cited

U.S. PATENT DOCUMENTS

| | | | |
|---|---|---|---|
| 3,366,971 A | * 2/1968 | Scherz | 2/412 |
| 3,507,727 A | * 4/1970 | Marshack | 156/153 |
| 3,552,044 A | 1/1971 | Wiele | |
| 4,338,371 A | * 7/1982 | Dawn et al. | 442/373 |
| 4,455,684 A | 6/1984 | Johnson | |
| 4,534,068 A | 8/1985 | Mitchell et al. | |
| 4,558,470 A | * 12/1985 | Mitchell et al. | 2/414 |
| 4,610,034 A | * 9/1986 | Johnson | 2/459 |
| 4,808,469 A | * 2/1989 | Hiles | 428/318.6 |
| 5,083,361 A | * 1/1992 | Rudy | 29/454 |
| 5,098,421 A | 3/1992 | Zook | 604/367 |
| 5,165,752 A | * 11/1992 | Terry | 297/214 |
| 5,200,256 A | * 4/1993 | Dunbar | 428/212 |
| 5,274,846 A | * 1/1994 | Kolsky | 2/460 |
| 5,423,087 A | * 6/1995 | Krent et al. | 2/463 |
| 5,741,568 A | * 4/1998 | Rudy | 428/69 |
| 5,930,840 A | * 8/1999 | Arai | 2/411 |
| 6,149,617 A | * 11/2000 | McNally et al. | 602/62 |
| 6,467,099 B2 | * 10/2002 | Dennis et al. | 2/455 |
| 6,653,363 B1 | * 11/2003 | Tursi et al. | 521/174 |
| 2002/0002730 A1 | * 1/2002 | Dennis et al. | 2/411 |
| 2002/0152542 A1 | * 10/2002 | Dennis et al. | 2/414 |

\* cited by examiner

*Primary Examiner*—Kim M. Lewis
(74) *Attorney, Agent, or Firm*—Jon M. Dickinson, P.C.; Robert D. Varitz, P.C.

(57) ABSTRACT

A topographically self-stabilizing, dynamic pressure-evenizing, pressure-applying, anatomical dressing which includes a pressure-applying, acceleration-rate-sensitive, temperature and pressure responsive, cushioning layer which responds during a bandaging situation, both statically and dynamically, to maintain relatively uniform all-over pressure beneath it, and against the surface of a site, such as a surgical wound site.

6 Claims, 2 Drawing Sheets

PRESSURE-EVENIZING LOW-REBOUND WOUND DRESSING

BACKGROUND AND SUMMARY OF THE INVENTION

This invention relates to structure usable for bandaging, such as bandaging of a wound area of the anatomy of a living subject Very specifically, it relates to a structure which enables bandaging of such an area, whereby the region bandaged and engaged by the structure of this invention is subjected to substantially an even and uniform, dynamically adaptable, overall pressure, without the existence of any appreciable high-pressure or low-pressure contact points.

It is well known that with respect to the healing of various wounds, such as those that result from surgical procedures, it is important that various fluid flows into and through the healing wound area, such a blood flow in that area, be allowed to continue substantially normal flow-behavior, in order to speed the healing process. It is also important in many instances to prevent the potentially problematic build-up of pooled, excess fluid in pockets under the skin.

Conventional bandaging approaches, however, do not often achieve ideal pressure-applying conditions. Very specifically, it is common in prior art practice that a the pressure-applying bandage will not properly, and most desireably, topographically follow the underlying contours of the anatomy, and will end up applying high pressure to certain regions, such as regions overlying a blood vessel, which elevated pressure will tend to constrict blood flow during the bandaging period, and thus prolong the healing process. Additionally, conventional bandaging which ends up applying overpressure in certain covered areas, also often ends up in applying underpressure in adjacent regions which then can promote the unwanted pooling of excess fluid in these regions. This overpressure/underpressure behavior is undesirable.

The present invention addresses these issues in a very satisfactory and practical manner by employing a bandaging structure which utilizes a low-spring-rate, compressible/flowable material, such as a viscoelastic material, which is a temperature and pressure responsive, acceleration-rate-sensitive material. Such a specialized-characteristic material, which, under compression in a bandaging situation, has been discovered to conform itself adaptively to the underlying bandaged anatomy, and even dynamically with respect, for example, to pulsatile topographic behavior, such as is common near a blood vessel where blood flows in a pulsatile manner. Such dynamic adaptation performance results in the underlying bandaged area being subjected to a substantially uniform, overall pressure—or at least a pressure area-distribution which does not constrict the normal flow of body fluids, such as blood. Topographic conformation as just outlined, aided by adjacent body temperature and bandaging compression, also deals very effectively with the matter of excess pooling of subcutaneous fluids.

Another type of fluid management condition which is important in certain bandaging situations involves bandaging relative to the lymph system. The bandaging structure of the present invention, just as it deals with pulsatile blood flow behavior of the category generally outlined above, also responds with like accommodation to behavior in and near the lymph system during a period of bandaging.

Preferably, that surface of the mentioned low-spring-rate cushioning material which directly faces the bandaging region on the anatomy is coated, or otherwise appropriately covered, with a thin layer of a moisture-barriering material. Such a material prevents any weeping wound fluid from working its way into the cushioning material, and perhaps thereby diminishing that material's important pressure-evenizing and dynamic behaviors just discussed. However, there may also be situations in which moisture barriering is not a requirement, and in these circumstances, an embodiment of the invention which does not include an extra moisture-barrier layer may very readily and successfully be employed.

These and other objects and feature and advantages that are offered by the present invention will become more fully apparent as the description which now follows is read in conjunction with the accompanying drawings.

DESCRIPTION OF THE DRAWINGS

FIG. 2 further illustrates how this device performs when the overall bandaging structure is applied to a topographically uneven wound area on the anatomy.

It should be noted that components of the invention shown in these drawings are not drawn to scale.

DETAILED DESCRIPTION OF THE INVENTION

Figure 1:
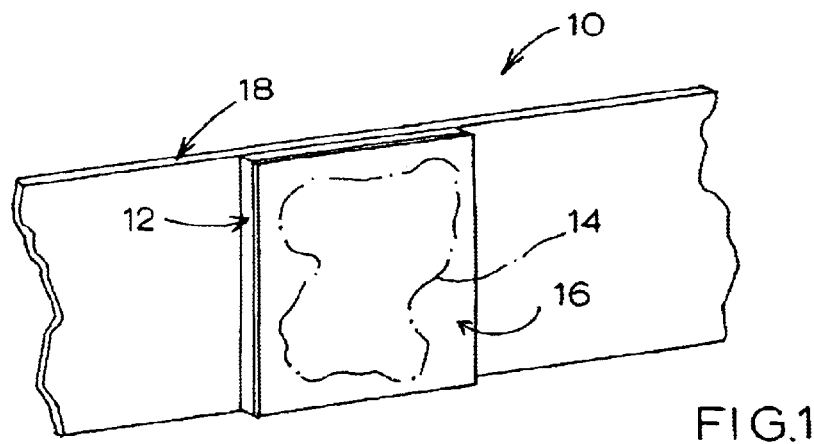
FIG. 1 is a simplified, isometric, fragmentary view of one embodiment of a simple anatomical bandaging or dressing structure constructed in accordance with the present invention.
Figure 2:
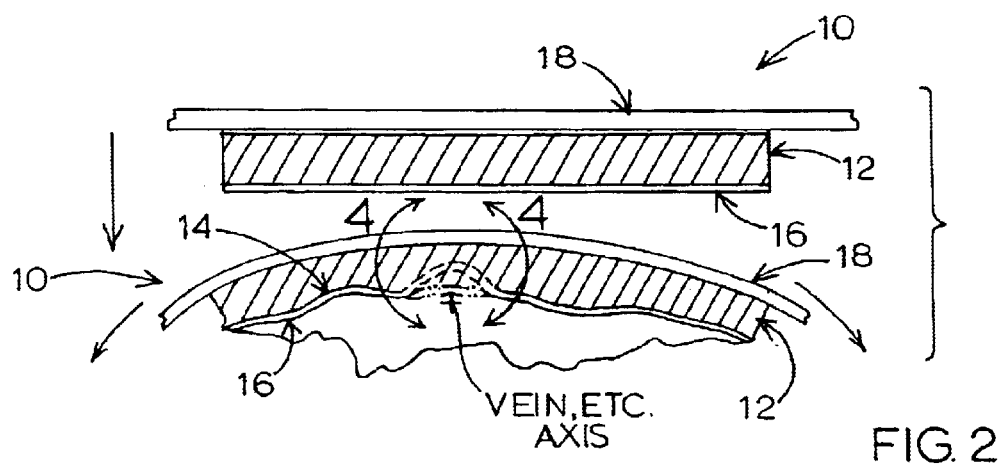
FIG. 2 is an enlarged, fragmentary two-condition edge view of the bandaging device pictured in FIG. 1.

Turning attention now to the drawings, and referring first of all to FIGS. 1 and 2, indicated generally at 10 is an anatomical dressing suitable for wound bandaging and made in accordance with a preferred embodiment of the present invention. Included in dressing 10, in the form of a layer 12, is an expanse of an appropriate acceleration-rate-sensitive viscoelastic material which is pictured in FIGS. 1 and 2 as a rectangle. The perimeter size and outline of layer 12 which define its area are completely matters of choice, and the thickness of this layer lies preferably about in the range of about 0.5- to about 1.5-inches. Very specifically, the dressing pictured in FIGS. 1 and 2 is shaped and sized, so-to-speak, to be usable to apply bandaging pressure to a wound area on the anatomy of a person, such wound area being illustrated schematically and just very generally by the irregular dash-dot line 14. While various acceleration-rate-sensitive materials may be employed herein, one that has been found to be particularly effective is a viscoelastic material designated as Confor CF-40, made by a company called EAR Specialty Composites in Indianapolis, Ind. Other similar viscoelastic materials may also be used, and if desired, plural stacked, and slightly differentiated layers may also be used.

Appropriately joined to that face of layer 12 which faces the viewer in FIG. 1, and which is the downwardly facing face in FIG. 2, is a thin layer, typically about 0.003- to about 0.01-index, of a suitable moisture-barriering material 16 which is made herein of a sprayed-on layer formed of a vinyl-solvent-based material known as Russell Coating, sold under the product designator V-2000, and manufactured by Russell Products Company, Inc., at 275 N. Forge Street, Akron, Ohio 44304. In the embodiment of the invention now being described, it is the exposed facial expanse specifically of material 16 which substantially directly engages, in most instances, the surface area of the wound area to which bandaging pressure is applied by device 10.

Finally included in the device pictured in FIGS. 1 and 2 is a securing strap, or band structure, 18 which is appropriately joined to the rear surface of layer 12 as such is viewed in FIG. 1. A material which might typically be employed here is any conventional elastomeric or non-elastomeric bandaging/strapping material. A rigid binder structure could also be employed for this purpose in certain applications., and opposite end regions of this material, not shown in the drawings, are prepared for suitable coupling, as through a hook-and-pile type fastening structure.

Figure 4:
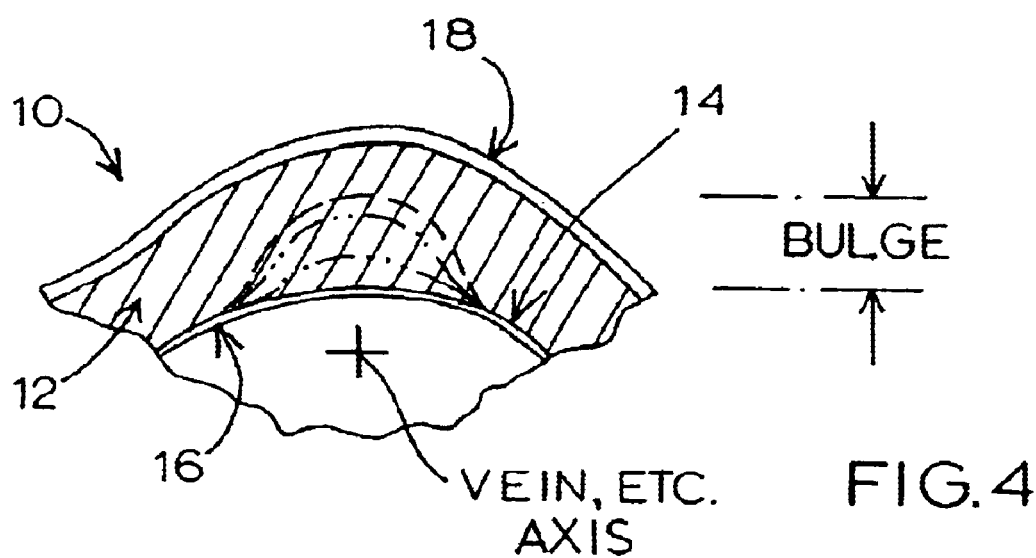
FIG. 4 is an enlarged, fragmentaiy detail which illustrates both static and dynamic performance of the invention as pictured in FIG. 2 in the region identified by curved, double-headed arrows 4—4 in FIG. 2.

The lower portion of FIG. 2, which should now be read along with what is shown in FIG. 4, clearly illustrates both the static and the dynamic bandaging behaviors offered specially by device 10. The region of the anatomy which is bandaged by device 10 is generally shown at 14, and one can see that this area is here pictured with a quite uneven, undulating topography. Specifically also illustrated in FIGS. 2 and 4, and underlying the surface of this anatomical site as is indicated by a cross pictured in FIGS. 2 and 4, is a pulsatile blood-flow artery or vein. This region of the anatomy is especially distortedly emphasized in FIGS. 2 and 4 in order aid in explaining and visualizing an important behavioral operation of the invention. An exaggerated BULGE is shown and so labeled in FIG. 4.

In dashed lines in FIGS. 2 and 4, this particular area of site 14 in the anatomy is shown distended, or bulged, upwardly to follow a line which is pictured as a dashed line in FIGS. 2 and 4. This region, under such a circumstance, is clearly a candidate for the undesirable applying of overly high pressure in a normal bandaging arrangement, but not under circumstances when it is bandaged by device 10, as pictured in FIGS. 2 and 4. This specific region is considered herein, for illustration purposes, to be a pulsatile region, and thus the outward bulging or projection changes in a periodic manner with respect to pulse flow of blood beneath the skin surface in this region. Dash-double-dot and dash-triple-dot lines in FIG. 4 generally picture different conditions of extension or distension of this region as a consequence of the pusatile activity taking place beneath the skin surface. A vein, etc. axis is shown as a cross.

Uniquely, and because of the acceleration-rate-sensitive nature of layer 12, when device 10 is appropriately placed to apply pressure to wound area 14, the skin-facing surface region of layer 12 adjusts its topographical characteristics so as to produce, ideally, a substantially matching complementary topography—and very specifically a matching topography which tends to produce a generally evenized pressure over the entirety of site 14.

Thus, from a purely static pressure-applying point of view, the portion of device 10 which acts through layers 12, 16 directly over wound site 14 tends to adjust so as to apply appropriate topographically-following, relatively even pressure such that undesirable overpressure and underpressure conditions mentioned above do not come into play.

From a dynamic point of view, and in response to pulsatile behavior as pictured in FIGS. 2 and 4, the acceleration-rate-sensitive material in layer 12 tends to respond to increased bulging (as a consequence of periodic blood flow) to yield, and when bulging begins to recede, to follow that receding activity with little or no appreciable spring-rate behavior, A consequence of this is that, even in a dynamic pulsatile region in a bandaging site, the device of this invention tends to adapt appropriately and easily to changing topographic conditions, and specifically in a manner tending to maintain substantially even overall bandaging pressure.

The moisture-barriering layer guards layer 12 from the invasion of any weeping fluid near the wound site.

Figure 3:
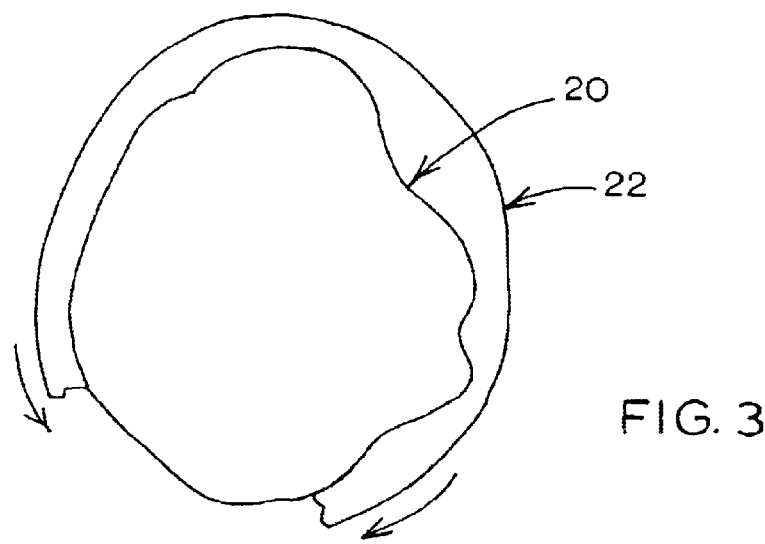
FIG. 3 is a very simplified, cross-sectional view taken through a person's knee structure to illustrate a wrap-around type bandaging application implemented by the present invention, which application offers pressure-evenizing behavior.

Turning attention for a moment to FIG. 3, here, in a very simple manner, there is illustrated at 20 the cross-sectional configuration of a person's knee. Here, also, the specific perimetral outline of this cross section is somewhat exaggerated in terms of its uneven undulation characteristic.

Figure 5:
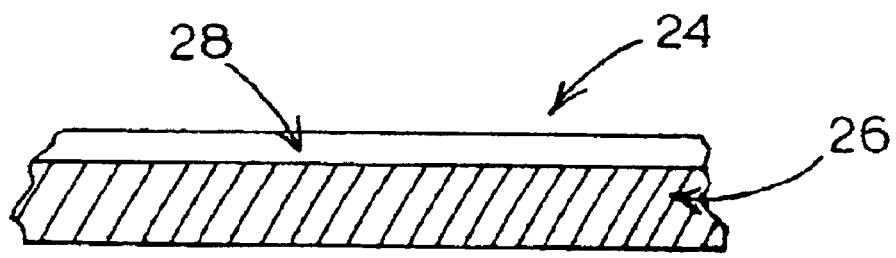
FIG. 5 is a fragmentary layer-edge view of a modified form of the invention wherein no moisture-barriering film, or layer, is employed.

Applied as a wrap-around bandaging structure is a device 22 which, except perhaps for specific size and facial outline, is substantially the same as previously described device 10. For simplicity, the several specific layers that make up device 22, and which are functionally the same layers pictured for device 10, are not shown in detail in FIG. 3. However, what is very clearly shown is the fact that the inwardly directed facial expanse of device 22 which directly engages the perimetral surface of the knee region tends to follow the topography of that knee region quite exactly, and in a manner, due to acceleration-rate-sensitive performance, causing it to apply substantially uniform pressure on and around the bandaged area. Obvious regions around the knee as shown in FIG. 3 are potential candidates for unwanted high-pressure and low-pressure conditions, but device 22 avoids these conditions, Finally, now, turning to FIG. 5, here there is shown at 24 a modified form of the invention which merely includes a cushioning layer 26, which is like cushioning layer 12, a securing structure 28, which is like securing structure 18, but no moisture-barriering layer. Were such a barriering layer to be presented in his modification, that layer would appear at the base of the structure specifically pictured in FIG. 5. It is the lower portion of device 24 as shown at FIG. 5 which provides the bandaging and pressure-applying expanse that is directed immediately toward and facing a wound site, such as wound site 14. This embodiment is preferably employed in a bandaging situation where fluid weeping is not expected to be an issue.

In addition to the clear pressure-applying features and advantage offered by the present invention, another positive contribution which is made involves cushioning and load-dispersion under circumstances where the outside surface of the bandaging structures comes inadvertently in contact with a sharp or point-load type object with an unexpected blow, and in relation to other kinds of potentially discomforting outside contacts.

Accordingly, a preferred embodiment, and a modification of the invention have been described herein, each of which offers all of the pressure-applying advantages discussed hereinabove. Thus, and while certain embodiments of the invention have been expressly pictured and discussed herein, it is appreciated that other variations and modifications may be made without departing from the sprit of the invention.

We claim:

1. A topographically self-stabilizing, dynamic pressure-evenizing, medical pressure-applying, anatomical dressing for use over a selected bandaging area comprising, a cushioning layer possessing an expanse having an area which is suitable for spanning, and thus covering, sigh a selected bandaging area on the anatomy of a living subject, said cushioning layer being formed of a compressible, non-springy, acceleration-rate-sensitive material which, after a compression deformation, exhibits a slow creep return toward an undeformed condition, and securing structure operatively joined to said expanse, adapted for securing the expanse to the anatomy in a manner overlying and applying desired pressure to the selected bandaging area.

2. The dressing of claim 1, wherein said cushioning layer includes a surface intended to face the bandaging area, and suitably joined to that surface is an overlayer of a moisture-barrier layer material.

3. The dressing of claim 1, wherein said acceleration-rate-sensitive material is also temperature and pressure responsive.

4. A topographically self-stabilizing, dynamic pressure-evenizing, medical pressure-applying, anatomical dressing comprising an acceleration-rate-sensitive cushioning layer possessing an expanse having an area which is suitable for spanning, and thus covering, a selected bandaging area on the anatomy of a living subject, and securing structure operatively joined to said expanse adapted to secure the expanse to such anatomy in a manner overlying and applying desired pressure to the selected bandaging area.

5. The dressing of claim 4, wherein said cushioning material comprises a viscoelastic material.

6. The dressing of claim 4, wherein, one surface of said cushioning layer expanse is covered by a layer of a moisture-barrier material.

* * * * *

UNITED STATES PATENT AND TRADEMARK OFFICE
CERTIFICATE OF CORRECTION

| | |
|---|---|
| PATENT NO. | : 6,812,375 B2 |
| APPLICATION NO. | : 10/174886 |
| DATED | : November 2, 2004 |
| INVENTOR(S) | : Michael R. Dennis et al. |

Page 1 of 1

It is certified that error appears in the above-identified patent and that said Letters Patent is hereby corrected as shown below:

Column 4, line 67, "sigh" should read --such--

Signed and Sealed this

Seventeenth Day of March, 2009

JOHN DOLL
*Acting Director of the United States Patent and Trademark Office*